United States Patent [19]

Wulff

[11] Patent Number: 4,539,561

[45] Date of Patent: Sep. 3, 1985

[54] PROCESS AND DEVICE FOR INSPECTING THE SURFACE OF A MATERIAL

[75] Inventor: Gunther Wulff, Stein am Rhein, Switzerland

[73] Assignee: Swiss Aluminium Ltd., Chippis, Switzerland

[21] Appl. No.: 464,049

[22] Filed: Feb. 4, 1983

[30] Foreign Application Priority Data

Feb. 15, 1982 [CH] Switzerland .............................. 924/82

[51] Int. Cl.³ .............................................. G08B 21/00
[52] U.S. Cl. .................................................... 340/675
[58] Field of Search ......................... 340/540, 675, 691; 73/105; 358/106; 356/430; 250/562, 563

[56] References Cited

U.S. PATENT DOCUMENTS 3,786,265  1/1974  Abilock et al. ................... 250/562
4,253,113  2/1981  Decavel et al. .................. 358/106
4,417,149 11/1983  Takeuchi et al. ................. 250/563

Primary Examiner—Anthony V. Ciarlante
Attorney, Agent, or Firm—Bachman and LaPointe

[57] ABSTRACT

The surface of a material is inspected for defects by visual examination of a television picture of the surface produced by at least one camera focused on the material and transmitting an image to a screen in the form of a video signal. The connection between screen and camera is made only when a defect is detected on the surface of the material. The video signal is delimited by an upper and a lower signal level which, if exceeded, results in a trigger signal being activated. In addition a trigger mechanism and an image storage facility are provided between the screen and the camera. Appearing on the screen are only pictures of surface areas showing defects; areas without defects are not displayed on the screen.

15 Claims, 2 Drawing Figures

PROCESS AND DEVICE FOR INSPECTING THE SURFACE OF A MATERIAL

BACKGROUND OF THE INVENTION

The invention relates to a process for checking the surface of a material, in particular cast aluminum strip, by visual inspection of an image of the material surface provided by at least one camera monitoring the material and supplying the image to a screen via a video signal. The invention also relates to a device for this purpose.

Known so-called on-line quality control methods are carried out for example using magnetic scattering, ultrasonics, induction currents, or also in a trivial manner by visual inspection of the surface of the material by an observer. Today considerable use is made of television so that the surface is imaged either as a whole or in part and displayed on one or more TV monitors. By freezing the image briefly stationary pictures are obtained of the moving material. By selecting TV cameras of specific spectral sensitivity (e.g. in the infra red range) and by filtering the incident light it is possible to optimize the contrast of the colored picture for ease of recognition of a fault by the observer. The linear scanning of a TV picture permits a computerized record of surface defects by comparison with standards; this can then be processed to register commands for sorting or control for treatment of the surface.

The advantages of the optical methods lie in their applicability to items at any elevated temperature. The optical method enables the avoidance of wear or damage to detectors by the moving item thanks to the large camera-object distance which can be selected. In additon, they have the ability to image the whole or the greater part of the surface of interest instead of the spot or linear inspection possible with all other methods.

On the other hand it is a disadvantage that this surface inspection is possible only at relatively slow strip speeds. At higher speeds only individual parts are displayed as a stationary picture, which then permits only partial inspection e.g. 20% of the total surface area.

The faster the movement of the strip, the poorer and less often are the flaws detected.

SUMMARY OF THE INVENTION

It is therefore an object of the invention to overcome these disadvantages and to develop a system of quality control which is simple and as economic as possible, and such that the cameras and TV monitor screens available up to now can be readily used.

This object is achieved by way of the invention whereby the connection between screen and camera is made only when a defect is detected on the material.

To this end the video signal is delimited within an upper and lower signal strength beyond which the video signal activates a trigger signal for a freely variable duration $\tau$. Between two trigger signals the image of the defect is held on the monitor screen by means of an image storage facility such as a video-recorder. This storage facility also has such a large capacity that it can store one or more successive images. This method has the great advantage that only pictures of areas featuring flaws appear on the screen while defect-free lengths of strip do not generate any pictures. As a result no unnecessary demands are made of the concentration of the observer.

Furthermore, the material e.g. a cast strip can run at relatively high speed as a stationary picture is displayed only if and when a surface defect appears. As defects do not occur very frequently, all defects are, as a rule, correctly and accurately assessed. The picture remains displayed on the screen until the camera senses a new surface defect.

BRIEF DESCRIPTION OF THE DRAWINGS

Further advantages, features and details of the invention are revealed in the following descrption of a preferred exemplified embodiment and with the help of drawings viz.

DETAILED DESCRIPTION

Figure 2:
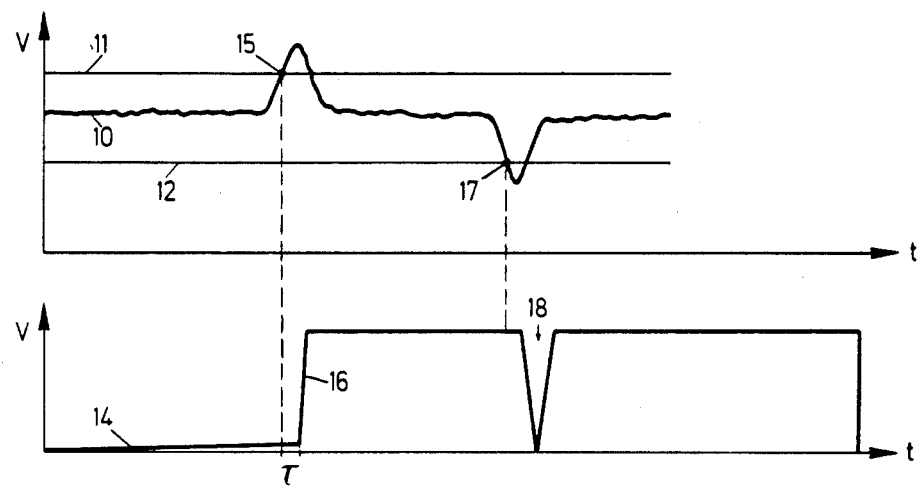
FIG. 2: A diagram of a video signal along with a diagram of a trigger signal corresponding to the video signal.
Figure 1:
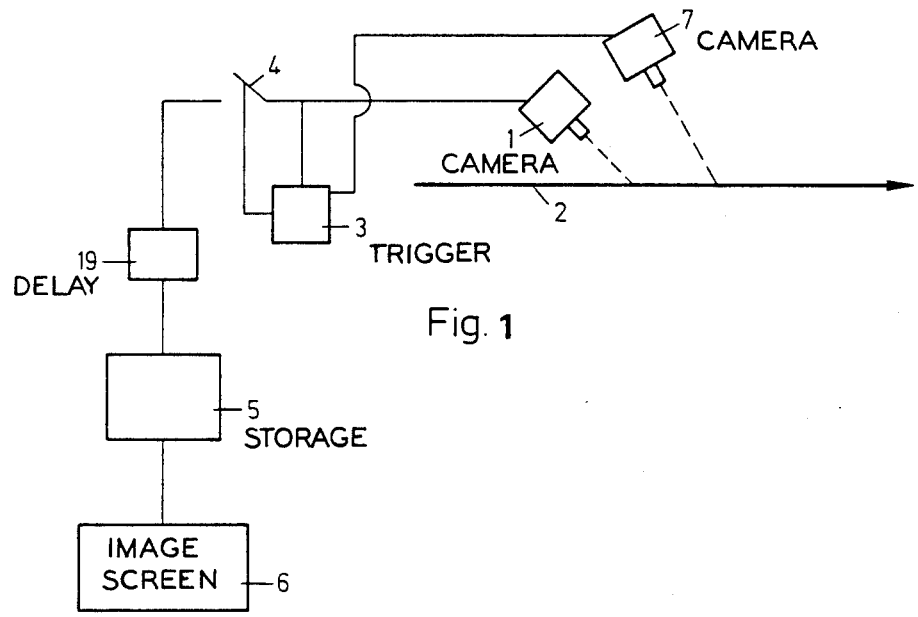
FIG. 1: A schematic representaton of a facility for inspecting the surface of a material.

In accordance with the present invention, preferably the image storage facility has capacity for a plurality of successive pictures which can be called up on demand so that a new defect does not immediately cause the earlier defect image to be removed from the screen.

Furthermore, in accordance with the invention, a delay facility is provided between the trigger switch and the image storage device, by means of which an image displayed as a result of triggering of the system can be projected on a monitor at other downstream positions. This produces a displacement of the image on the monitor with respect to the point of origin of the defect.

Also, the trigger mechanism can be connected to a second camera by means of which an image displaced with respect to that taken by the first camera can be registered and fed to the image storage facility. This too considerably improves the recognition of defects and in particular the evaluaton of these.

A preferred device for performing the process according to the invention is such that a trigger mechanism and an image storage facility are provided between the screen and the camera.

With this arrangement it is possible to install, displaced with respect to the first camera, a second camera which takes a picture displaced with respect to that taken by the first camera.

Usefully a delay facility is provided between the trigger mechanism and the image storage facility.

The storage facility is usually of the FIFO (first in first out) type with a capacity for one or more successive images.

As a rule known inspection facilities already have a camera and a screen, therefore it is sufficient to install between these facilities a storage facility and a trigger mechanism along with a delay facility as an extra instrument.

Referring to the drawings, a video camera 1 televises the surface of a cast strip 2 and controls a trigger mechanism 3 which is connected to an image storage facility 5 via a switch 4. The storage facility 5 is preferably fitted with a selection device. The material stored by the storage facility 5 can be imaged on screen 6.

A delay facility 19 is provided between the trigger mechanism 3 and the storage facility 5.

Connected to the trigger mechanism is optionally a second video camera 7 to televise a part of the strip displaced with respect to that taken by the first camera 1.

As shown in FIG. 2 a video signal 10 occupies a range within an upper level 11 and a lower level 12. Defects on the cast strip 2 produce a deviation in the video signal 10 as a result of which the signal 10 enters the range beyond levels 11 or 12. In the present example the video signal 10 activates a trigger signal 14. At point 15 the video signal 10 exceeds the upper level 11. After a freely selectable time $\tau$ this produces the trigger impulse 16 which leads to the connection being made between camera 1 and image storage facility 5. This picture remains on display until, as a result of the lower level 12 being crossed at point 17, the command is given to record the next image via a second trigger impulse 18.

What is claimed is:

1. Process for inspection of the surface of a material by visual examination of a television picture produced by at least one camera focused on the material surface and displaying the resultant image obtained on a monitor or screen, which comprises: providing the surface of a material to be inspected, providing a camera focused on said surface operative to detect defects on said surface and a screen operatively connected to said camera, providing means for displaying said surface on said screen only when said camera detects a defect on the surface of the material.

2. Process according to claim 1 wherein said surface is a cast aluminum strip.

3. Process according to claim 1 wherein a video signal is transmitted from said camera delimited by an upper and a lower signal level which, if exceeded, results in a trigger signal being activated to display said surface on said screen.

4. Process according to claim 3 including a storage facility operatively connected between said screen and camera, wherein the image of the defect is held on the screen between a first trigger signal and a second trigger signal with the help of said image storage facility.

5. Process according to claim 4 wherein the image storage facility stores one or more successive, complete pictures.

6. Process according to claim 3 wherein the pictures projected as a result of triggering are projected on the monitor at another, downstream position by means of a delay facility between the trigger and the storage facility.

7. Process according to claim 3 including a second camera operatively connected to said screen, wherein an image displaced with respect to that taken by the first camera is taken by said second camera and is fed to the image storage facility via the trigger signals.

8. Process according to claim 1 wherein said surface is a moving strip.

9. Device for inspection of the surface of a material by visual examination of television picture produced by at least one camera focused on the material surface and displaying via a video signal the resultant image of the material surface on a monitor or screen, which comprises a surface of a material to be inspected, a camera focused on said surface operative to detect thereon, a screen operatively connected to said camera, and means between said camera and screen for transmitting the video signal and thereby displaying said surface on said screen only when a defect is detected on the surface by said camera.

10. Device according to claim 9 wherein said means includes a trigger mechanism between said camera and screen.

11. Device according to claim 10 including an image storage facility between said trigger mechanism and screen.

12. Device according to claim 11 including a delay facility between the trigger mechanism and image storage facility.

13. Device according to claim 11 wherein the image storage facility is a FIFO (first in first out) type with a capacity for one or more pictures.

14. Device according to claim 9 including a second camera offset from said first camera and operatively connected to said screen for televising the strip and producing an image displaced with respect to that taken by the first camera.

15. Device according to claim 9 wherein said surface is a moving strip.

* * * * *